United States Patent
Lee et al.

(10) Patent No.: US 6,180,827 B1
(45) Date of Patent: *Jan. 30, 2001

(54) RECOVERY OF ACRYLIC ACID FROM PROCESS OR WASTE WATER STREAMS

(75) Inventors: Fu-Ming Lee, Katy; Ronald G. Gualy, Houston, both of TX (US)

(73) Assignee: HFM International, Inc., Houston, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/229,873

(22) Filed: Jan. 14, 1999

Related U.S. Application Data

(63) Continuation of application No. 09/229,873, filed on Jan. 14, 1999
(60) Provisional application No. 60/073,501, filed on Feb. 3, 1998.

(51) Int. Cl.[7] ................................................ C07C 51/42
(52) U.S. Cl. ............................................ 562/600; 562/513
(58) Field of Search ................................ 562/600, 513

(56) References Cited

U.S. PATENT DOCUMENTS

| | | | |
|---|---|---|---|
| 3,932,500 | * 1/1976 | Duembgen et al. | 562/600 |
| 3,997,599 | * 12/1976 | Grinstead | 562/513 |
| 4,576,683 | * 3/1986 | Cohen | 203/15 |
| 5,399,751 | 3/1995 | Gentry et al. | 562/608 |
| 5,409,579 | 4/1995 | Gualy et al. | 203/16 |
| 5,492,603 | 2/1996 | Gualy et al. | 202/158 |
| 5,492,625 | 2/1996 | Wytcherley et al. | 210/634 |
| 5,624,566 | 4/1997 | Wytcherley et al. | 210/634 |
| 5,746,892 | 5/1998 | Bauer, Jr. et al. | 203/38 |
| 5,759,358 | 6/1998 | Bauer, Jr. et al. | 203/38 |

FOREIGN PATENT DOCUMENTS

| | | |
|---|---|---|
| 0 551 111 | 7/1993 | (EP) . |
| 0 685 448 | 12/1995 | (EP) . |
| 0 695 736 | 2/1996 | (EP) . |
| 0 770 592 | 5/1997 | (EP) . |
| 0 778 255 | 6/1997 | (EP) . |

* cited by examiner

Primary Examiner—Paul J. Killos
Assistant Examiner—Taylor V. Oh
(74) Attorney, Agent, or Firm—Jenkens & Gilchrist, A Professional Corporation

(57) ABSTRACT

Disclosed is a method for recovering acrylic acid from process or waste water streams in which the stream is vaporized and contacted with a liquid high boiling solvent for acrylic acid, thereby absorbing acrylic acid into the solvent. Mixed trialkylphosphine oxides are a preferred solvent. Acrylic acid is stripped from the solvent with heat and, optionally, stripping gas. It may be separated from any accompanying materials to produce acrylic acid of high purity.

31 Claims, 2 Drawing Sheets

RECOVERY OF ACRYLIC ACID FROM PROCESS OR WASTE WATER STREAMS

This application is a continuation application claiming priority from copending application Ser. No. 09/229,873, filed Jan. 14, 1999, which is a utility application based on and claiming the benefit of provisional Application Ser. No. 60/073,501, filed Feb. 3, 1998.

SUMMARY OF THE INVENTION

This invention is related to a novel absorption process for recovering acrylic acid from an acrylic acid-containing process or waste water stream. In this process, a high boiling liquid solvent is used to contact a vapor feed stream containing acrylic acid, in a counter-current or co-current fashion in a column. The column normally contains trays or packings to facilitate the necessary vapor and liquid contact, allowing acrylic acid to be absorbed by the solvent.

For example, the lean (liquid) solvent can be fed near the top the column, while the vapor feed stream can enter the column near the bottom of the column. As the lean solvent flows down through the column, it contacts the upcoming vapor stream and preferentially absorbs acrylic acid from the vapor stream. The rich (acrylic acid-laden) solvent exits the column at the bottom, while the acrylic acid-removed vapor stream exits at the top the column.

The rich solvent is then fed to the middle portion of a solvent stripper where acrylic acid is stripped from the solvent by heat alone, or heat in combination with stripping nitrogen. Acrylic acid is withdrawn from the top of the stripper as the product or as the subject for farther purification. The lean solvent from the bottom of the stripper is recycled back to the absorption column for reuse.

In accordance with a preferred embodiment of the invention, the high boiling liquid solvent is a phosphine oxide solvent, such as CYANEX 923 manufactured by Cytec Corporation, and is used as the absorption solvent in the invention. It is a mixture of four trialkylphosphine oxides, and has a reported composition as follows:

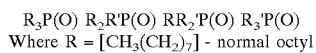
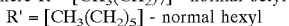

Where R = [CH$_3$(CH$_2$)$_7$] - normal octyl
R' = [CH$_3$(CH$_2$)$_5$] - normal hexyl
Average Molecular Weight = 348 (approximately)
Typical properties of this solvent are reported as follows:

| | |
|---|---|
| Trialkylphosphine oxides | 93% |
| Appearance | Colorless mobile liquid |
| Specific Gravity | 0.88 at 23° C. |
| Freezing Point | −5 to 0° C. |
| Viscosity | 40.0 centipoise at 25° C. |
| | 13.7 centipoise at 30° C. |
| Flashpoint | 182° C. |
| (Closed Cup Setaflash) | |
| Autoignition Temperature | 218° C. |
| Vapor Pressure | 0.09 mm Hg at 31° C. |
| Boiling Point | 310° C. at 50 mm Hg |
| Solubility in Water | 10 mg/l |
| Solubility of Water in CYANEX 923 extractant | 8 wt % |

When in this specification and in the accompanying claims the term 'solvent consisting essentially of mixed trialkylphosphine oxides' is used, the material referred to is that just described and characterized above, and its equivalents.

The non-limiting solvents for this invention also include dialkyl alkyl phosphinates, alkyl dialkyl phosphinates, trialkyl phosphine oxides, dialkyl alicyclic amidophosphates, dialkyl sulfoxides, tetra-alkyl ureas, sulfones (including sulfolane), glycols (including tetraethylene glycol), pyrrolidones (including N-methyl pyrrolidone and 2-pyrrolidone), morpholines (including N-formyl morpholine), acetamides (including dimethyl acetamide), formamides (including dimethyl formamide), tertiary amines, etc.

DESCRIPTION OF PREFERRED EMBODIMENTS

The advantages of the present invention are more clearly described in the following examples but they do not limit it in any way.

EXAMPLE 1

Figure 1:
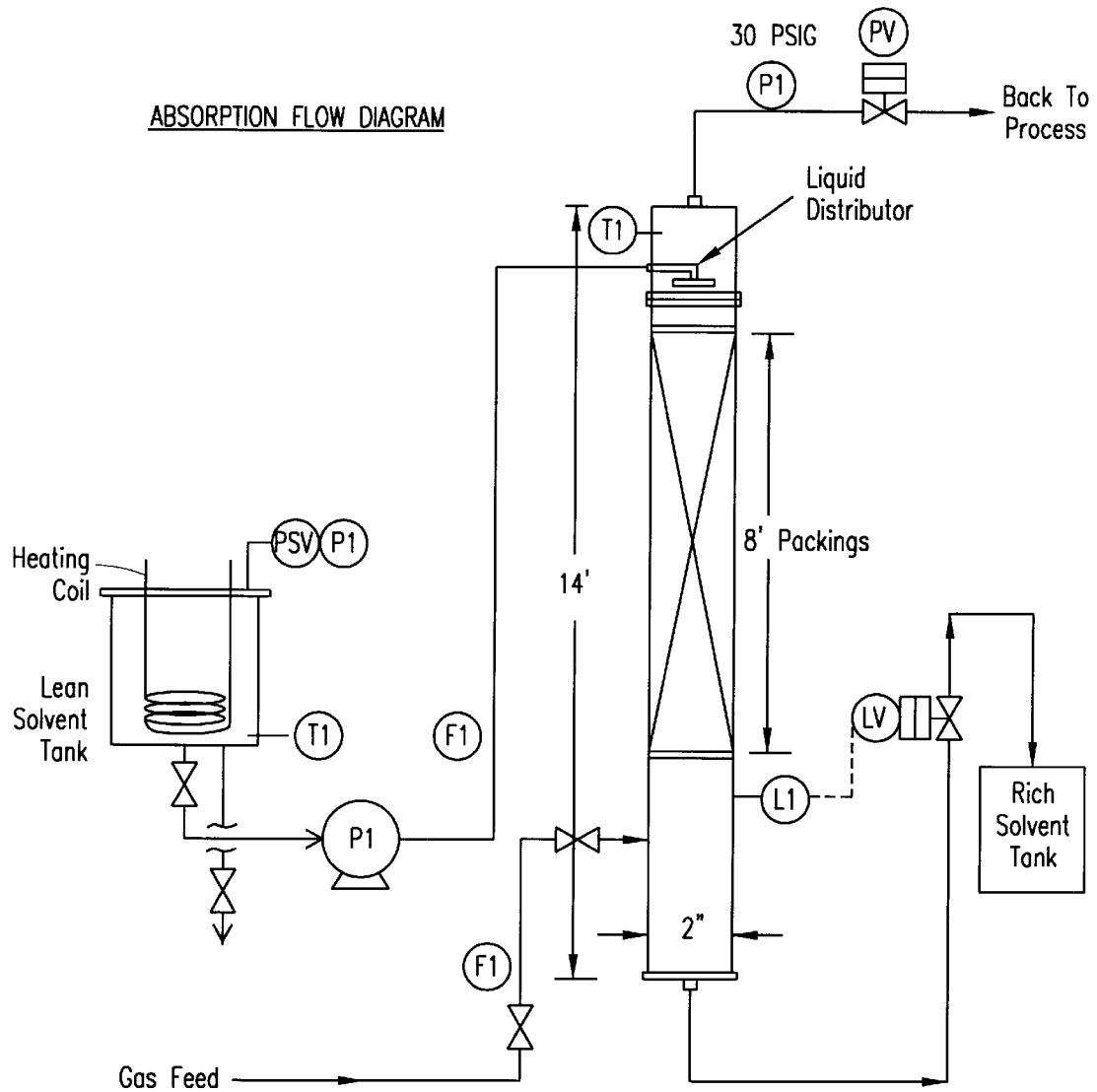
FIG. 1 is a schematic diagram for an absorption test column in accordance with the invention.

Test runs were conducted in a stainless steel absorption column 2-inches in diameter and 14 feet high packed with 8 feet of structured packings. A schematic diagram of this absorption column is shown in FIG. 1. A vapor feed stream withdrawn from a commercial acrylonitrile reactor was fed to a point near the bottom of the absorption column. The vapor feed composition is given in Table 1.

TABLE 1

| Component | Weight percent |
|---|---|
| CO | 0.96 |
| $CO_2$ | 2.47 |
| $N_2$ | 62.20 |
| $NH_3$ | 0.40 |
| $O_2$ | 1.49 |
| Propane | 0.04 |
| Propylene | 0.30 |
| HCN | 1.89 |
| Acrolein | 0.15 |
| Acrylonitrile | 11.57 |
| Acetonitrile | 0.53 |
| $H_2O$ | 17.64 |
| Acetic acid | 0.02 |
| Acrylic acid | 0.26 |

The vapor feed stream was contacted counter-currently with mixed trialkylphosphine oxides liquid solvent (CYANEX 923 ), which was fed to a point near the top of the column. The product vapor stream was withdrawn from the top of the column. The acrylic acid content in the feed and the product vapor streams were analyzed simultaneously during the operation. The column was operated according to the following conditions:

Solvent/feed ratio: 15–50 gallons /1000 CFM

Absorption temperature: 200–210° C.; 170–180° C.; 130–140° C.

Gas velocity in column: 5 ft/sec (about 7 CFM vapor feed rate)

Pressure: 0.6 Kg/cm$^2$ (gage)

The results are summarized in Table 2.

TABLE 2

| Temperature (° C.) | Acrylic acid in vapor feed stream (kg/hr) | Acrylic acid in vapor product streams (kg/hr) | % of Acrylic Acid Absorbed |
|---|---|---|---|
| 200–210 | 307 | 19 | 93.7 |
| 200–210 | 290 | 19 | 93.4 |
| 200–210 | 201 | 8 | 96.1 |
| 200–210 | 266 | 16 | 94.2 |
| 200–210 | 269 | 23 | 91.4 |
| 170–180 | 286 | 10 | 96.6 |
| 170–180 | 228 | 6 | 97.4 |
| 170–180 | 286 | 6 | 98.0 |
| 130–140 | 276 | 4 | 98.6 |
| 130–140 | 267 | 4 | 98.5 |
| 130–140 | 205 | 4 | 98.1 |

As shown in Table 2, the percent of absorption figures at various temperatures are very high, even at temperatures as high as 200 to 210° C.

EXAMPLE 2

Based on the experimental results demonstrated in Example 1, in accordance with the invention, a process scheme was developed for commercial applications. The schematic process flow diagram is presented in FIG. 2.

Figure 2:
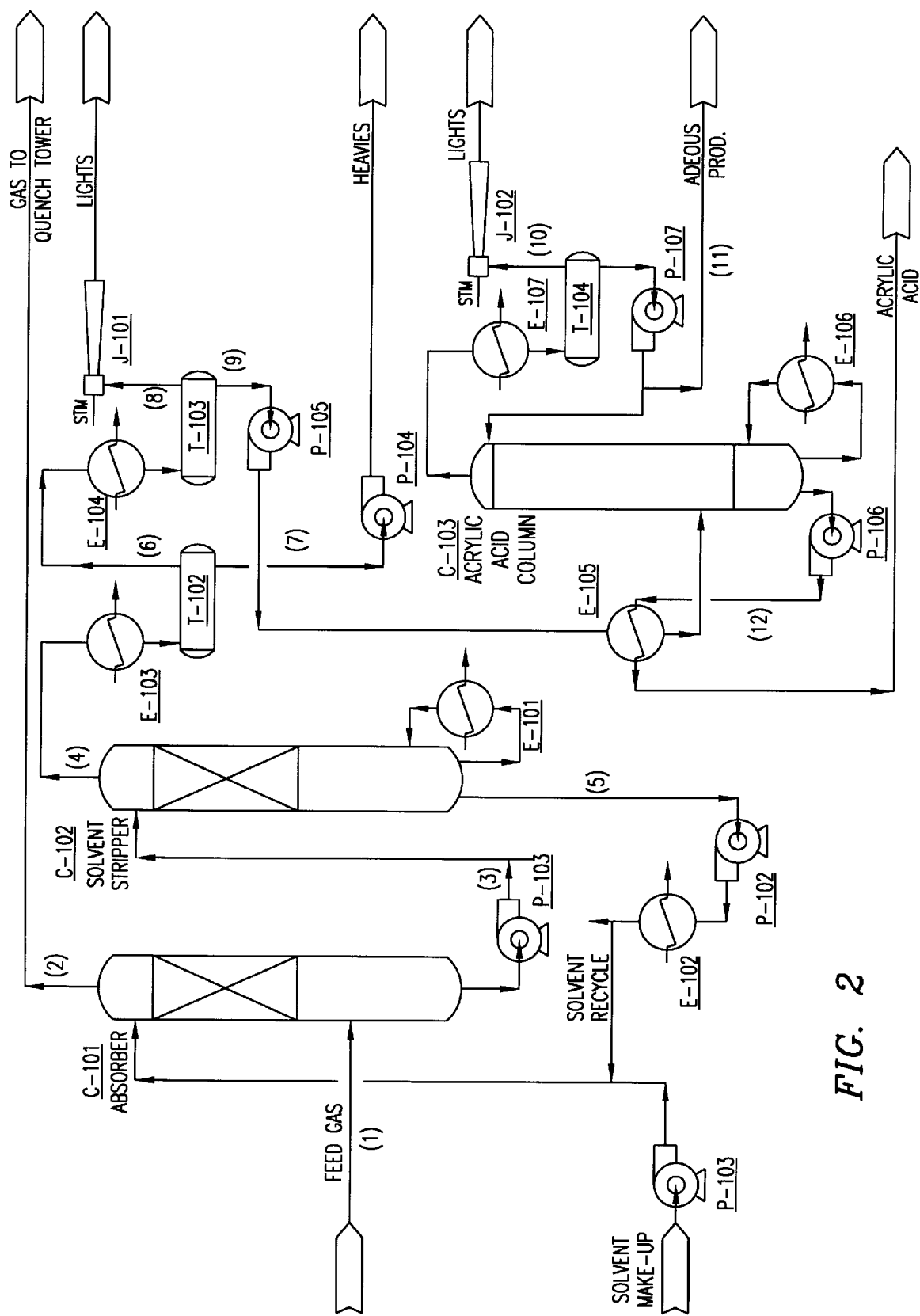
FIG. 2 is a schematic diagram for a commercial process in accordance with the invention.

According to FIG. 2, the effluent from an acrylonitrile reactor (207,118 lbs/hr), containing 0.26 wt % acrylic acid is fed to Absorber C-101 through Line 1. The stream is contacted with 22,742 lbs/hr of CYANEX 923 solvent counter-currently in Absorber C-101. Approximately 80% of the acrylic acid is absorbed by the solvent exiting at the bottom of the C-101 via Line 3, while the vapor stream with acrylic acid largely removed exits at the top of the column for further processing in the acrylonitrile plant.

The bottoms stream is fed through to Solvent Stripper C-102 where the absorbed acrylic acid is stripped from the solvent by heat or heat plus stripping gas such as nitrogen. The lean solvent (22,742 lbs/hr) is recycled through Line 5 to Absorber C-101 for reuse. The stripped stream (2,596 lbs/hr) containing 16.7 wt % acrylic acid is withdrawn from C-102 via Line 4 and cooled by Cooler E-103 before entering a liquid settler T-102 to remove the heavies (50 lbs/hr). The vapor stream leaving T-102 through Line 6 is further cooled by Cooler E-104 before entering liquid accumulator T-103 which is operated under vacuum to remove lights (1,378 lbs/hr) containing mainly nitrogen and acrylonitrile, to be recycled to the acrylonitrile plant. The liquid stream from T-103 (1,168 lbs/hr) with 36.4 wt % acrylic acid, 56.4 wt % water, 3 wt % acetic acid and minor amount of lights is sent to the acrylic acid column to distill off water, acetic acid and lights. The product acrylic acid (428 lbs/hr) at 95 wt % purity is withdrawn at the bottom of Column C-103 through Line 12. The detailed material balance figures for all process streams shown in FIG. 2 are presented in Table 3.

TABLE 3

| | 1 | | 2 | | 3 | | 4 | |
|---|---|---|---|---|---|---|---|---|
| | lbs/hr | wt % | lbs/hr | wt % | lbs/hr | wt % | lbs/hr | wt % |
| CO | 1989 | 0.96 | 1979 | 0.97 | 10 | 0.38 | 10 | 0.38 |
| $CO_2$ | 5128 | 2.48 | 5102 | 2.49 | 26 | 0.99 | 26 | 0.99 |
| $N_2$ | 128834 | 62.20 | 128190 | 62.68 | 644 | 24.82 | 644 | 24.82 |
| $NH_3$ | 820 | 0.40 | 812 | 0.40 | 8 | 0.32 | 8 | 0.32 |
| $O_2$ | 3078 | 1.49 | 3063 | 1.50 | 15 | 0.59 | 15 | 0.59 |
| Propane | 75 | 0.04 | 74 | 0.04 | 1 | 0.03 | 1 | 0.03 |
| Propylene | 611 | 0.30 | 605 | 0.30 | 6 | 0.24 | 6 | 0.24 |
| HCN | 3911 | 1.89 | 3872 | 1.89 | 39 | 1.51 | 39 | 1.51 |
| Acrolein | 315 | 0.15 | 312 | 0.15 | 3 | 0.12 | 3 | 0.12 |
| Acrylonitrile | 23966 | 11.57 | 23487 | 11.48 | 479 | 18.47 | 479 | 18.47 |
| Acetonitrile | 1096 | 0.53 | 1074 | 0.53 | 22 | 0.84 | 22 | 0.84 |
| Methacrylonitrile | 130 | 0.06 | 33 | 0.02 | 98 | 3.76 | 98 | 3.76 |
| $H_2O$ | 36526 | 17.64 | 35795 | 17.50 | 731 | 28.14 | 731 | 28.14 |
| Acetic Acid | 44 | 0.02 | 9 | 0.00 | 35 | 1.36 | 35 | 1.36 |
| Acrylic Acid | 542 | 0.26 | 108 | 0.05 | 434 | 16.71 | 434 | 16.71 |
| Nicotinonitrile Solvent | 53 | 0.03 | 8 | 0.00 | 45 | 1.74 | 45 | 1.74 |
| Total lbs/hr | 207118 | 100.00 | 204522 | 100.00 | 2596 | 100.00 | 2596 | 100.00 |
| Moles, lbmols | 7581 | | 7496 | | 85 | | 85 | |

| | 5 | | 6 | | 7 | | 8 | |
|---|---|---|---|---|---|---|---|---|
| | lbs/hr | wt % | lbs/hr | wt % | lbs/hr | wt % | lbs/hr | wt % |
| CO | 0 | 0.00 | 10 | 0.39 | 0 | 0.00 | 10 | 0.73 |
| $CO_2$ | 0 | 0.00 | 26 | 1.02 | 0 | 0.00 | 26 | 1.89 |
| $N_2$ | 0 | 0.00 | 644 | 25.30 | 0 | 0.00 | 644 | 46.72 |
| $NH_3$ | 0 | 0.00 | 8 | 0.31 | 0 | 0.00 | 8 | 0.58 |
| $O_2$ | 0 | 0.00 | 15 | 0.59 | 0 | 0.00 | 15 | 1.09 |
| Propane | 0 | 0.00 | 1 | 0.04 | 0 | 0.00 | 1 | 0.07 |
| Propylene | 0 | 0.00 | 6 | 0.24 | 0 | 0.00 | 6 | 0.44 |
| HCN | 0 | 0.00 | 39 | 1.53 | 0 | 0.00 | 39 | 2.83 |
| Acrolein | 0 | 0.00 | 3 | 0.12 | 0 | 0.00 | 3 | 0.22 |
| Acrylonitrile | 0 | 0.00 | 479 | 18.81 | 0 | 0.00 | 455 | 33.01 |
| Acetonitrile | 0 | 0.00 | 22 | 0.86 | 0 | 0.00 | 20 | 1.44 |

TABLE 3-continued

|  |  |  |  |  |  |  |  |  |
|---|---|---|---|---|---|---|---|---|
| Methacrylonitrile | 0 | 0.00 | 98 | 3.85 | 0 | 0.00 | 78 | 5.69 |
| H$_2$O | 0 | 0.00 | 731 | 28.71 | 0 | 0.00 | 73 | 5.30 |
| Acetic Acid | 0 | 0.00 | 34 | 1.35 | 1 | 1.41 | 0 | 0.00 |
| Acrylic Acid | 0 | 0.00 | 425 | 16.69 | 9 | 17.37 | 0 | 0.00 |
| Nicotinonitrile | 0 | 0.00 | 5 | 0.18 | 41 | 81.22 | 0 | 0.00 |
| Solvent | 22742 | 100.00 |  |  |  |  |  |  |
| Total lbs/hr | 22742 | 100.00 | 2546 | 100.00 | 50 | 100.00 | 1378 | 100.00 |
| Moles, lbmols | 65 |  | 84 |  | 1 |  | 41 |  |

What is claimed is:

1. A method for recovering acrylic acid from an acrylic acid-containing vapor stream comprising:
   contacting said vapor stream with a liquid high boiling solvent for acrylic acid selected from the class consisting of mixed trialkyl phosphine oxides, dialkyl alkyl phosphinates, alkyl dialkyl phosphinates, trialkyl phosphine oxides, dialkyl alicylic amidophosphates, dialkyl sulfoxides, sulfones, sulfolane, glycols, tetraethylene glycol, and mixtures thereof, thereby absorbing acrylic acid into said solvent to form rich solvent; and
   stripping acrylic acid from said rich solvent to thereby recover it.

2. A method in accordance with claim 1 in which the source of said acrylic acid-containing vapor stream is a process or waste water stream and further comprising vaporizing said acrylic acid-containing process or waste water stream to form said acrylic acid-containing vapor stream.

3. A method in accordance with claim 1 in which said vapor stream and said liquid solvent are contacted in counter-current flow.

4. A method in accordance with claim 1 in which said stripping of acrylic acid from said rich solvent is performed by heating said solvent.

5. A method in accordance with claim 4 and further in which a stripping gas is passed through said rich solvent to aid in stripping acrylic acid therefrom.

6. A method in accordance with claim 1 in which lean solvent resulting from said stripping of said rich solvent is recycled to contact additional vapor containing acrylic acid.

7. A method in accordance with claim 1 in which lean solvent resulting from said stripping of said rich solvent is recycled to contact additional vapor containing acrylic acid.

8. A method in accordance with claim 7 in which said acrylic acid stripped from said rich solvent is separated from any materials accompanying it by forming a second vapor stream of acrylic acid and accompanying materials, cooling said second vapor stream to condense and thereby separate from it relatively heavy accompanying materials, further cooling said second vapor stream to condense from it acrylic acid, water, acetic acid, and other accompanying materials, leaving a vapor stream containing nitrogen and acrylonitrile, and distilling the condensed acrylic acid, water, acetic acid and other accompanying materials to thereby recover acrylic acid of high purity.

9. A method for recovering acrylic acid from an acrylic acid-containing vapor stream comprising:
   contacting said vapor stream with a liquid high boiling solvent for acrylic acid selected rom the class consisting of pyrrolidones, N-methyl pyrrolidone, morpholines, N-formyl morpholine, acetamides, dimethyl acetamide, formamides, dimethyl formamide, tertiary amines, and mixtures thereof; and
   stripping acrylic acid from said rich solvent to thereby recover it.

10. A method in accordance with claim 9 in which the source of said acrylic acid-containing vapor stream is a process or waste water stream and further comprising vaporizing said acrylic acid-containing process or waste water stream to form said acrylic acid-containing vapor stream.

11. A method in accordance with claim 9 in which said vapor stream and said liquid solvent are contacted in counter-current flow.

12. A method in accordance with claim 9 in which said stripping of acrylic acid from said rich solvent is performed by heating said solvent.

13. A method in accordance with claim 12 and further in which a stripping gas is passed through said rich solvent to aid in stripping acrylic acid therefrom.

14. A method in accordance with claim 9 in which lean solvent resulting from said stripping of said rich solvent is recycled to contact additional vapor containing acrylic acid.

15. A method in accordance with claim 9 in which acrylic acid stripped from said rich solvent is separated from water and organic materials accompanying it to produce high purity acrylic acid.

16. A method in accordance with claim 15 in which said acrylic acid stripped from said rich solvent is separated from any materials accompanying it by forming a second vapor stream of acrylic acid and accompanying materials, cooling said second vapor stream to condense and thereby separate from it relatively heavy accompanying materials, further cooling said second vapor stream to condense from it acrylic acid, water, acetic acid, and other accompanying materials, leaving a vapor stream containing nitrogen and acrylonitrile, and distilling the condensed acrylic acid, water, acetic acid and other accompanying materials to thereby recover acrylic acid of high purity.

17. A method for using a liquid high boiling solvent for acrylic acid selected from the class consisting of mixed trialkyl phosphine oxides, dialkyl alkyl phosphinates, alkyl dialkyl phosphinates, trialkyl phosphine oxides, dialkyl alicylic amidophosphates, dialkyl sulfoxides, sulfones, sulfolane, glycols, tetraethylene glycol, and mixtures thereof, to recover acrylic acid from an acrylic acid-containing vapor stream comprising:
   contacting said vapor stream with said liquid high boiling solvent, thereby absorbing acrylic acid into said solvent to form rich solvent; and
   stripping acrylic acid from said rich solvent to thereby recover it.

18. A method in accordance with claim 17 in which the source of said acrylic acid-containing vapor stream is a process or waste water stream and further comprising vaporizing said acrylic acid-containing process or waste water stream to form said acrylic acid-containing vapor stream.

19. A method in accordance with claim 17 in which said vapor stream and said liquid solvent are contacted in counter-current flow.

20. A method in accordance with claim 17 in which said stripping of acrylic acid from said rich solvent is performed by heating said solvent.

21. A method in accordance with claim 20 and further in which a stripping gas is passed through said rich solvent to aid in stripping acrylic acid therefrom.

22. A method in accordance with claim 17 in which lean solvent resulting from said stripping of said rich solvent is recycled to contact additional vapor containing acrylic acid.

23. A method in accordance with claim 22 in which said acrylic acid stripped from said rich solvent is separated from any materials accompanying it by forming a second vapor stream of acrylic acid and accompanying materials, cooling said second vapor stream to condense and thereby separate from it relatively heavy accompanying materials, further cooling said second vapor stream to condense from it acrylic acid, water, acetic acid, and other accompanying materials, leaving a vapor stream containing nitrogen and acrylonitrile, and distilling the condensed acrylic acid, water, acetic acid and other accompanying materials to thereby recover acrylic acid of high purity.

24. A method for using a liquid high boiling solvent for acrylic acid selected from the class consisting of pyrrolidones, N-methyl pyrrolidone, morpholines, N-formyl morpholine, acetamides, dimethyl acetamide, formamides, dimethyl formamide, tertiary amines, and mixtures thereof to recover acrylic acid from an acrylic acid-containing vapor stream comprising:

contacting said vapor stream with said high boiling solvent; and stripping acrylic acid from said rich solvent to thereby recover it.

25. A method in accordance with claim 24 in which the source of said acrylic acid-containing vapor stream is a process or waste water stream and further comprising vaporizing said acrylic acid-containing process or waste water stream to form said acrylic acid-containing vapor stream.

26. A method in accordance with claim 24 in which said vapor stream and said liquid solvent are contacted in counter-current flow.

27. A method in accordance with claim 24 in which said stripping of acrylic acid from said rich solvent is performed by heating said solvent.

28. A method in accordance with claim 27 and further in which a stripping gas is passed through said rich solvent to aid in stripping acrylic acid therefrom.

29. A method in accordance with claim 24 in which lean solvent resulting from said stripping of said rich solvent is recycled to contact additional vapor containing acrylic acid.

30. A method in accordance with claim 24 in which acrylic acid stripped from said rich solvent is separated from water and organic materials accompanying it to produce high purity acrylic acid.

31. A method in accordance with claim 30 in which said acrylic acid stripped from said rich solvent is separated from any materials accompanying it by forming a second vapor stream of acrylic acid and accompanying materials, cooling said second vapor stream to condense and thereby separate from it relatively heavy accompanying materials, further cooling said second vapor stream to condense from it acrylic acid, water, acetic acid, and other accompanying materials, leaving a vapor stream containing nitrogen and acrylonitrile, and distilling the condensed acrylic acid, water, acetic acid and other accompanying materials to thereby recover acrylic acid of high purity.

* * * * *